US009723251B2

(12) United States Patent
Slotky

(10) Patent No.: US 9,723,251 B2
(45) Date of Patent: Aug. 1, 2017

(54) TECHNIQUE FOR IMAGE ACQUISITION AND MANAGEMENT

(71) Applicant: Jaacob I. Slotky, Closter, NJ (US)

(72) Inventor: Jaacob I. Slotky, Closter, NJ (US)

( * ) Notice: Subject to any disclaimer, the term of this patent is extended or adjusted under 35 U.S.C. 154(b) by 454 days.

(21) Appl. No.: 14/211,047

(22) Filed: Mar. 14, 2014

(65) Prior Publication Data
US 2014/0313334 A1    Oct. 23, 2014

Related U.S. Application Data

(60) Provisional application No. 61/814,880, filed on Apr. 23, 2013.

(51) Int. Cl.
H04N 5/77 (2006.01)
H04N 5/232 (2006.01)
G01N 21/95 (2006.01)

(52) U.S. Cl.
CPC .......... H04N 5/77 (2013.01); G01N 21/9515 (2013.01); H04N 5/23222 (2013.01); *G01N 2201/0221* (2013.01)

(58) Field of Classification Search
USPC .......................... 348/148, 125–129, 133–136
See application file for complete search history.

(56) References Cited

U.S. PATENT DOCUMENTS

| | | | | |
|---|---|---|---|---|
| 7,453,559 B2 * | 11/2008 | Dorran | ............... | G01B 11/2755 356/139.01 |
| 9,208,384 B2 * | 12/2015 | Conwell | ........... | G06F 17/30265 |
| 2012/0249741 A1 * | 10/2012 | Maciocci | ................ | G06F 3/011 348/46 |
| 2012/0314916 A1 * | 12/2012 | Rothschild | ......... | G06K 9/00288 382/118 |
| 2013/0273968 A1 * | 10/2013 | Rhoads | ............. | G06F 17/30244 455/556.1 |
| 2013/0328762 A1 * | 12/2013 | McCulloch | .......... | G02B 27/017 345/156 |
| 2014/0171039 A1 * | 6/2014 | Bjontegard | ....... | H04L 29/06034 455/414.1 |
| 2014/0201126 A1 * | 7/2014 | Zadeh | .................... | G06K 9/627 706/52 |
| 2014/0254865 A1 * | 9/2014 | Soubra | ............... | G06K 9/00624 382/103 |

(Continued)

*Primary Examiner* — Paulos M Natnael
(74) *Attorney, Agent, or Firm* — Browdy and Neimark, PLLC

(57) ABSTRACT

A technique for image acquisition and management, by utilizing a mobile device equipped with a camera and a mobile software application. The software application enables a) providing guidance to an operator for making, by the camera, a set of one or more images of an object, so as to obtain them at one or more angles suggested by the software application for properly registering currently existing visible features of the object, b) obtaining the set of images, c) storing the set of obtained images as a current set, along with its related data, in at least one storage/processing location for further analysis. The technique, using the mobile software application, may also perform d) analysis of thus obtained current set of images by comparing it with another reference set of images of the same or similar object. The technique may be used, for example, for detecting defects on a vehicle body.

41 Claims, 3 Drawing Sheets

(56) References Cited

U.S. PATENT DOCUMENTS

2014/0267010 A1* 9/2014 Pasquero .............. G06T 19/006
    345/156
2014/0279242 A1* 9/2014 Staicut ............... G06Q 30/0643
    705/26.61

* cited by examiner

TECHNIQUE FOR IMAGE ACQUISITION AND MANAGEMENT

RELATED APPLICATIONS

This application claims priority from the U.S. provisional Patent Application No. 61/814,880 filed on Apr. 23, 2013.

FIELD OF THE INVENTION

The invention relates generally to the field of image acquisition, and more particularly relates to automated systems of visual defects detection.

BACKGROUND OF THE INVENTION

Among automated systems for detection of visual defects, techniques for car damage detection may serve a representative example.

Most of current damage assessment and reporting systems are based on the fact that the human eye is able to reliably detect and assess damage, if seen on a vehicle body, and record the results.

Some efforts have been made in the prior art to automate the process of car damage detection.

Various techniques of image comparison are available for the purpose of visual defects detection.

US2005125119 discloses a carriage that moves back and forth under a vehicle, and three cameras or a laser fixed along one axis pivot in a common plane, and teaches utilizing two cameras at time to locate a target fixed to a reference point on the undercarriage of the vehicle. Triangulation calculations, combined with the location of the cameras provide the location of the reference point in space in a three-dimensional coordinate system, compare that location with a stored designed location of the reference point prior to the crash, thus allowing the vehicle structure to be returned to its designed shape by other equipment.

US2006114531 describes methods, systems, and apparatuses for providing automated vehicle image acquisition, analysis, and reporting. One embodiment of the invention includes a method for providing vehicle damage information to an interested party. The method may include receiving simultaneously captured image data associated with a vehicle. The method can also include comparing at least a portion of the image data with previously stored image data associated with the vehicle. Furthermore, the method can include (based at least in part on the comparison of the portion of image data with previously stored image data associated with the vehicle), determining whether damage to the vehicle exists. In addition, the method can include outputting an indicator of whether damage to the vehicle exists.

US2007293997 describes a computer-assisted inspection system including an integrated software suite, which provides vehicle inspection services for various clients. The system provides customized workflow based on different inspection clients, different types of inspections and other factors. Different clients may have different inspection needs. Some clients may not care about certain defects that other clients want to know about. The system can provide, on the inspection appliance, different rules that can be activated in response to which client the inspection is being provided for and/or other factors for inspection criteria, valuation/pricing, rule-based validation and automatic grading. The resulting rule-driven user interface is thus customized-allowing the inspector to be more efficient in gathering the precise data desired at the time of data collection. Features include flat car part picking, highly client-customizability, easy to use, ability to run in an environment where the inspector has no constant connectivity to the network (no guaranteed access to the internet, full data replication, intermittent connectivity, synch back up), inspectors can be geographically separated (e.g., all over the country), system is installable over the internet to provide efficient installation to far-flung install sites.

OBJECT AND SUMMARY OF THE INVENTION

The Inventor has noticed and recognized a long felt need in a handy tool which—if existed—would be highly appreciated by each and every customer, salesperson, service provider who deals with products/items which may be changed/damaged during transportation, storage, use, wear etc. Such a customer may for example be a driver of a vehicle, a client or operator of auto rental, repair and insurance services.

To the best of the Applicant's knowledge, there is no information on applications for mobile devices such as smartphones, tablets, etc. that would guide an operator to gather proper images of a product/item (for example, of a vehicle body) for further processing thereof and/or for further use of the processed data in interaction with various product or service providers.

It is therefore one object of the present invention to provide such an application for mobile devices. One specific object of the invention is to provide a method of detecting damage/defects on a vehicle body, using the mentioned application. Still a further object of the invention is to provide a system for implementing such a method.

"Damage" or "defects" in terms of this patent should be understood as a visible trace of any change or discrepancy of a product's/item's external appearance, for example a visible trace of collision of a vehicle with an object, for example scratches or dents on the vehicle body. The term may also include replacement of an item with another one, traces of repairs of the previous damage, repainting of the vehicle body parts, etc.

Human eye is usually able to detect deformations of a car body while looking from a specific angle.

Therefore, an additional object of the invention is to provide a technique which would enable reliably detecting damage/defects visible to human eye or other computer vision assisted methods, and reporting such defects on a user's mobile device interface.

Yet a further object of the invention is providing a technique capable of reliably detecting defects (dents and/or scratches of varying sizes) on a vehicle body by simple means and by implementing a short procedure.

The invention will describe a technique initially intended for the guided image acquisition, storage and management, using a mobile device. The description of the technique below equally relates to a method, a system and a software product being elements of the technique.

The novel method/system/software application may further serve for analysis of possible changes of the object of interest. In one specific version, the method may be used for analysis of a vehicle body state and for detection of damages (if any).

According to a first aspect of the invention, there is provided a method for image acquisition and management, by utilizing a mobile device (smartphone, tablet or the like) equipped with a camera and with a mobile software application;

the method comprises the following steps enabled and/or supported by the software application:

providing guidance to an operator for making, by the camera, a set of one or more images of an object, so as to obtain said set of images using respective one or more angles (foreshortenings) suggested by the software application for properly registering currently existing visible features of said object, obtaining said set of images, storing said set of obtained images as a specific (for example, a current) reference set, along with its related data, in at least one storage/processing location being selected from a list comprising the mobile device and a remote location.

According to a slightly different aspect of the invention, there is provided a method for detecting differences/defects by utilizing said specific (current) reference set.

To this end, the method described above further comprises an operation of analysis including steps of:

comparing said specific (for example, current) reference set with an additional reference set, the additional reference set being selected from at least the following two additional reference sets:
an earlier reference set of said object,
a later reference set of said object;

based on said comparison, creating a report concerning differences, if any, between the obtained set of images being the specific reference set, and the selected additional reference set, displaying the report in at least one of said storage/processing locations.

When the guidance is performed based on the earlier reference set for said object, the earlier reference set and its corresponding related data is provided in advance and is accessible by said software application;

the guidance may then be aimed at obtaining said specific set of images being maximally close to the respective images in the earlier reference set, while said guidance is simultaneously aimed at properly registering the currently existing visible features of said object.

In other words, the guidance may be provided by directing the operator, via a display of the mobile device, to adjust an actual camera position and direction so as to maximally match the specific (current) reference set to the selected additional (earlier) reference set.

The earlier reference set may comprise one of the at least two following sets of images comprising one or more images provided before said specific reference set, and is accompanied with its related data:

a default/etalon set of one or more images created for objects of the type to which said object belongs;

a set of one or more images of said object, obtained (using said guidance or not, for example by a stationary camera) and stored in said at least one storage/processing location.

Generally, the additional reference set may be understood as:

a) a set of images of the same object (item/product/vehicle, etc.) taken at a different time (note that previously taken images may record some defects which existed in advance). Such an additional reference set may be obtained by a mobile device, using a similar inventive technique as described below, but may be provided in a different way, for example as described in b)

b) a set of images obtained by stationary camera/s (for example by camera/s of a parking lot, a garage, etc.) and stored in any suitable storage/processing location;

c) a set of suitable default/etalon images of the same object which may be obtained, for example, from a vehicle manufacturer. In one specific example, the reference set may be a set of images of a new vehicle of a the same type, model, color; they may be preliminarily provided either by the inventive technique or in a different manner, and stored either in the user's mobile device and/or in any other storage/processing location.

It should also be noted that the term "image" may be understood as a 2D or 3D image. In turn, the reference set may be understood as one or more 2D or 3D images, and in a specific example—as a 3D model of a vehicle of a particular make, model, color, possibly comprising 3D image(s) and a list of vehicle features.

Any of the reference sets (be they called a specific/current reference set or an additional reference set) obtained and stored as above may be used just for creating an inventory database. However, any of the reference sets may further be used for comparing it with another reference set of images (obtained for example in any of the ways listed above as a, b, or c, as an earlier or a later reference set of the same object).

Any of the reference sets may be obtained with a predetermined accuracy level, to allow further processing thereof.

In one specific version of the method, the object is a vehicle body. The method may serve for guided acquisition of images of a vehicle body, and/or for automatically detecting defects on the vehicle body, and displaying the report on said defects.

In other versions of the method, the object may be a human or an animal, wherein the method may be intended for obtaining and managing images for medical, cosmetic, prosecution and other purposes.

In still other versions of the method, the object may be an item or a product, and the method may be intended for obtaining and managing images to follow the object's changes during transportation, storage, exposure to light, rain, etc.

The method may further comprise
preliminarily creating/providing one or more said additional reference sets to be available to the mobile software application and/or a different storage/processing location,
selecting a particular additional reference set from said one or more additional reference sets for further processing.

Namely, based on the analysis of said specific/current set of images with one or more selected additional reference set/s, the method may create a report/reports concerning differences, if any, between the obtained current set of images and the selected one or more said additional reference sets, and may then display one or more of said reports.

If more than one report is created for the same object, the method may further comprise comparing said more than one report.

The related data (data related to one or another set of images) should be understood as comprising so-called meta-data for identifying said object, the place and/or time of taking images, etc.

The report should be understood as comprising at least said set of obtained images (forming the current reference set), accompanied by its related data and the analysis results. Optionally, the report may also comprise the additional reference set of images and its related data The method may comprise creating, for the same object, more than one such report respectively based on different more than one reference sets.

The operator may be understood as a user of the mobile device, a person providing services, a client receiving services, etc.

It should be understood that the step of creating the report may be performed in the mobile device and/or at any said storage/processing location; the step of displaying the report may also take place at any of such locations. Of course, the report may be stored at any of the storage/processing locations.

The term of a storage/processing location may be understood as the mobile device itself, or a remote location—for example a central location such as a central server intended for general computing services (such as "cloud" or the like), a central server providing to clients the described service according to the method, a computer, such as a local server of a company providing various conventional services (sales, transportation, rent, insurance, parking, etc.) to clients, or any combination of various storage/processing locations.

For example, the storage/processing location may be: a site and/or a server of a company authorized to assess damages of specific vehicles (for example, police, administrative institutions, trade companies, insurance agencies, rental services company, etc.), or the like. The set of images along with its related data, possibly also along with local processing/analysis data, may be transferred to such a location via communication lines, so that the images analysis and creation of the report may be performed there. It should be added that reports (comprising the images and the related data) may also be transmitted between different locations.

As mentioned, the guidance to the operator may be provided by directing the operator, via the display of the mobile device, to adjust an actual camera position and direction to maximally match the selected (additional) reference set.

For example, the guidance may be performed by positioning each image of the selected additional reference set as a transparent background on a display of the mobile device, when making a current image for said set of images (i.e., for the current reference set).

The method allows storing the acquired images and the related data locally (on the mobile device), and/or transferring (transmitting) it to another storage/processing location by means of a communication network.

An expanded version of the method may therefore comprise the following steps:
  providing the mobile device with said camera and said mobile software application,
  activating the mobile software application;
  obtaining said set of one or more images of the respective one or more portions of the object by using said camera with guidance of said mobile software application;
  storing the obtained set of images as a specific/current reference set in the mobile device and/or in a remote storage/processing location;
  selecting an additional reference set from one or more already available, earlier reference sets (available to the application and/or to any other storage/processing location),
    processing said current set of images by analyzing thereof based on the selected additional reference set,
  generating a report on differences between the current reference set and the selected additional reference set (the processing and the report generation can be performed by the application at the mobile device, and/or by computation means at any of said storage/processing locations);
  displaying, the report. As noted above, the report may be displayed on the mobile device and/or at a remote location, for example by means of an internet site.

As mentioned, the method may utilize a central storage/processing location, which may be a central server, a server of a dedicated company (say, providing support to software applications of the interested users who have the suitable software application installed in their mobile device), or a server of any other company (for example: vehicle rental, repair, trade, insurance, guard, legal, etc. services to the user)

The method may therefore further comprise a step of forwarding the obtained report to companies or institutions providing various services to the user, related to the object (for example, vehicle-related services). Correspondingly, a suitable software product (which will be described below) may be provided with a suitable capability of establishing communication with such companies/institutions for filing the report.

According to a second aspect of the invention, there is also provided a software product (e.g. a mobile software application for a mobile device such as a smartphone, a tablet, etc.) stored on an appropriate computer readable storage medium, comprising computer implementable instructions and/or data for carrying out the method disclosed in the present description, so that the software is capable of enabling operations of said method when used in a computer system.

In one specific and preferred embodiment, the storage medium is the memory of the mobile device, after the software application is downloaded from any other location where it is stored/marketed.

It should be noted however, that the functional block of the program product, which is responsible for the guided image acquisition, may be physically located at any storage location (in the mobile device, in a remote server, in both of them). In other words, the processing software may be distributed among multiple locations (one being the mobile device) and others may be one or many servers located centrally or in different geographic places.

In one specific embodiment, the software product may be a mobile software application for guided image acquisition and management, the software product being installable in a mobile device having a camera; the software application being designed for:
  providing guidance to an operator for making, by the camera, a set of one or more images of an object, so as to obtain said set of images using respective angles suggested by the software application for properly registering currently existing visible features of said object, thereby supporting the obtaining of said set of images by the operator, storing said set of obtained images, as a current reference set along with its related data, in at least one storage/processing location being selected from a list comprising the mobile device and a remote location.

Preferably, the software product is specifically designed for detecting defects on a vehicle body (i.e., wherein the object is a vehicle body).

Alternatively or in addition, the mobile software application may be capable of:

automatically analyzing said current reference set based on an additional reference set selected from those available in at least one storage/processing location from said list, based on said analysis, creating a report concerning differences, if any, between the current reference set and the additional reference set;

displaying the report in at least one storage/processing location from said list.

The guidance which gives the application may be for example by directing the user, via the display of the mobile device, to adjust an actual camera position and direction to maximally match the selected additional reference set (e.g., the previous images taken of the same vehicle, a set of suitable default images used as the reference, etc.)

The operations of processing, analysis may be performed by computational facilities at any of the mentioned storage/processing locations, separately or in parallel, and the report may be obtained at the mobile device either locally, or via communication means.

As mentioned above, the method may comprise a preliminary step of selecting or creating the mentioned "additional" reference set. Usually (but not mandatory) the additional reference set is an earlier obtained one.

To perform that, the software application may be adapted to guide the operator (user, etc.) for creating such a reference set.

In one specific version, the application may be capable of assisting the user to gather multiple images of the object (for example, of a vehicle body) in two periods of time, for the purpose to detect differences (such as surface features, defects, etc.) by comparing the actual/new images to suitable previous/old images. Alternatively, the comparison may be performed by comparing two reports: for example, a previously stored report and a current report. Reports usually comprise attached suitable images. Actually, comparison of reports may implicitly comprise comparison of the images by features extraction analysis, where the comparison is based on the features found in the reference set and in the inspected set of images. The comparison of images is usually accompanied by comparison of their related data.

For example, the software application may also be capable to enable identifying surface features of a vehicle based on the previously gathered and stored images of the same vehicle, comparing them with new suitable images of that vehicle and analyzing differences there-between.

As mentioned above, the at least one additional reference set may be selected from a list comprising at least:

a) a default set of corresponding images of a suitable new vehicle (i.e., a vehicle of the same model, the same color, etc. being free of defects), b) a previously obtained and stored set of corresponding images of the same vehicle, for example obtained according to the proposed method.

c) a model of the vehicle, such as a 3D model formed using 3D image/s. The mobile application (and/or computational facilities at another storage/processing location) may thus be adapted to detect any defects: "new", "old" or "all" ones, and will be capable of distinguishing between "old" defects and "new" defects.

One or more reference sets of the type b) may be stored. Each of such references may be obtained by making and storing said one or more images using guidance of the mobile software application, while also providing the related data, such as: identification of the object (for example, of the vehicle), indications of time and place (for example, a GPS position) of taking the images, coordinates of the images on the vehicle body, etc. At least one of such reference sets is a later reference set for the preceding one.

Any reference set, being it a current or an additional reference comprising a set of images obtained according to the invention, should be stored with its related data comprising unique identification of the object (say, a vehicle). The data may be retrieved, presented, or processed later, when the need appears.

According to yet a further aspect of the invention, there is provided a system for implementing the proposed method.

The system may comprise a mobile device with said software application installed in its memory. It will be the minimal system, since if one current reference set is created by the user and stored in the device, a further set of photos may be then compared with the stored reference (which will be considered the additional/earlier one) and the report may be generated by the software application.

However, the system may comprise cloud services, in which the software is hosted in a hardware provided by a third party (e.g., Amazon cloud) and the resources of the hardware are shared.

Also, as has been mentioned above, the software may run on multiple computers.

The system may comprise a storage/processing server at a remote (for example, central) location, connected with the mobile device via communication lines.

The system may further comprise a server or an internet site of an associated service company or other institution: such as an object (for example, a vehicle) manufacturer, a suitable shop, a rental company for renting suitable objects, garage, police, etc.), and suitable communication lines between the software application of the mobile device and the suitable company/institution.

The remote/central storage/processing location may be associated with location of servers of the mentioned companies/institutions.

One particular and important advantage of the invented method/system/software application is that the technique allows usage of simple user accessible tools by the operator, and without any dedicated hardware.

The invention will be further described in details as the description proceeds.

BRIEF DESCRIPTION OF THE DRAWINGS

The invention will be further described with reference to the following non-limiting drawings in which.

DETAILED DESCRIPTION OF THE INVENTION

Figure 1:
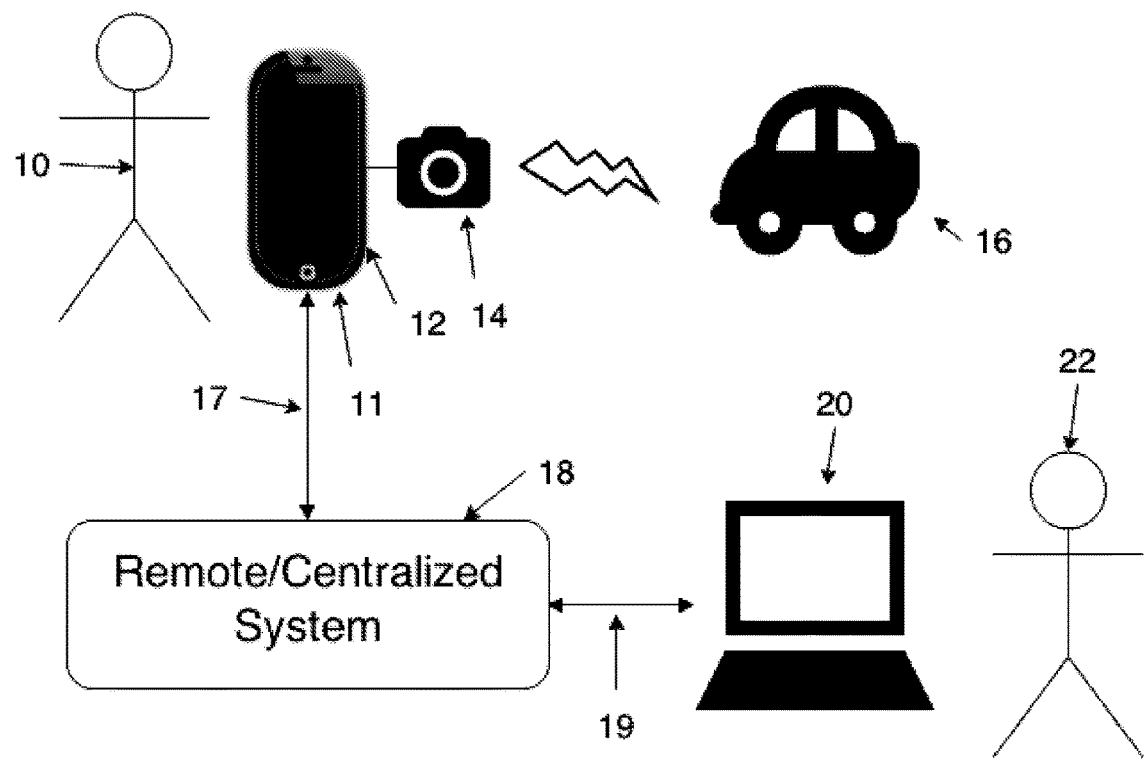
FIG. 1—is a simplified block diagram of an exemplary system for performing the proposed method.

FIG. 1 shows one embodiment of a system for implementing the proposed method. The simplest inventive system is in the upper part of the drawing, it comprises a mobile device 12 provided with a mobile software application 11 and a camera 14. The device 12 is operated by an operator 10 to take photographs of an object 16 (for example, of a car body) and, in the simplest version of the system, the software application 11 of the device 12 guides the user to take the photographs and stores them in the device 12 as a current reference set. Preferably, the software application 11 further analyzes external appearance of the object 16, based on a so-called additional reference set which may be provided to the application 11 in one or another manner, and then displays a report on the mobile device.

The inventive system may also comprise an optional part shown in the lower part of the drawing. The optional part comprises a remote (for example, centralized) processing/storage location or system 18 being connected via a communication line 17 with the mobile device 12, and via a communication line 19—to a computer/display 20 of the same or another remote location. The system 18 may be a web server application or a general server application designed, inter alia, for: storing suitable (current and additional/earlier) reference(s), receiving data (with or without the reference/s, with or without the reports) from the device 12, processing the received data and also for generating reports (if required) on differences of the external appearance of the object 16 from the mentioned additional reference(s).

The computer 20 is a conventional computer which may form part of the optional portion of the system, namely may be a server of a company providing services related to the object (for example, a manufacturer, a transportation company, an insurance company, a rental company, a shop, a police, etc.). A person 22 is a user/operator, which may participate in the process (for example, a sales person, a dispatcher, a policeman, a user renting a car, etc.). The operator 22 is provided with access to the storage/processing location 18 via the computer/server 20, and thus may be informed about report(s) generated/stored therein with respect to the object 16

Figure 2:
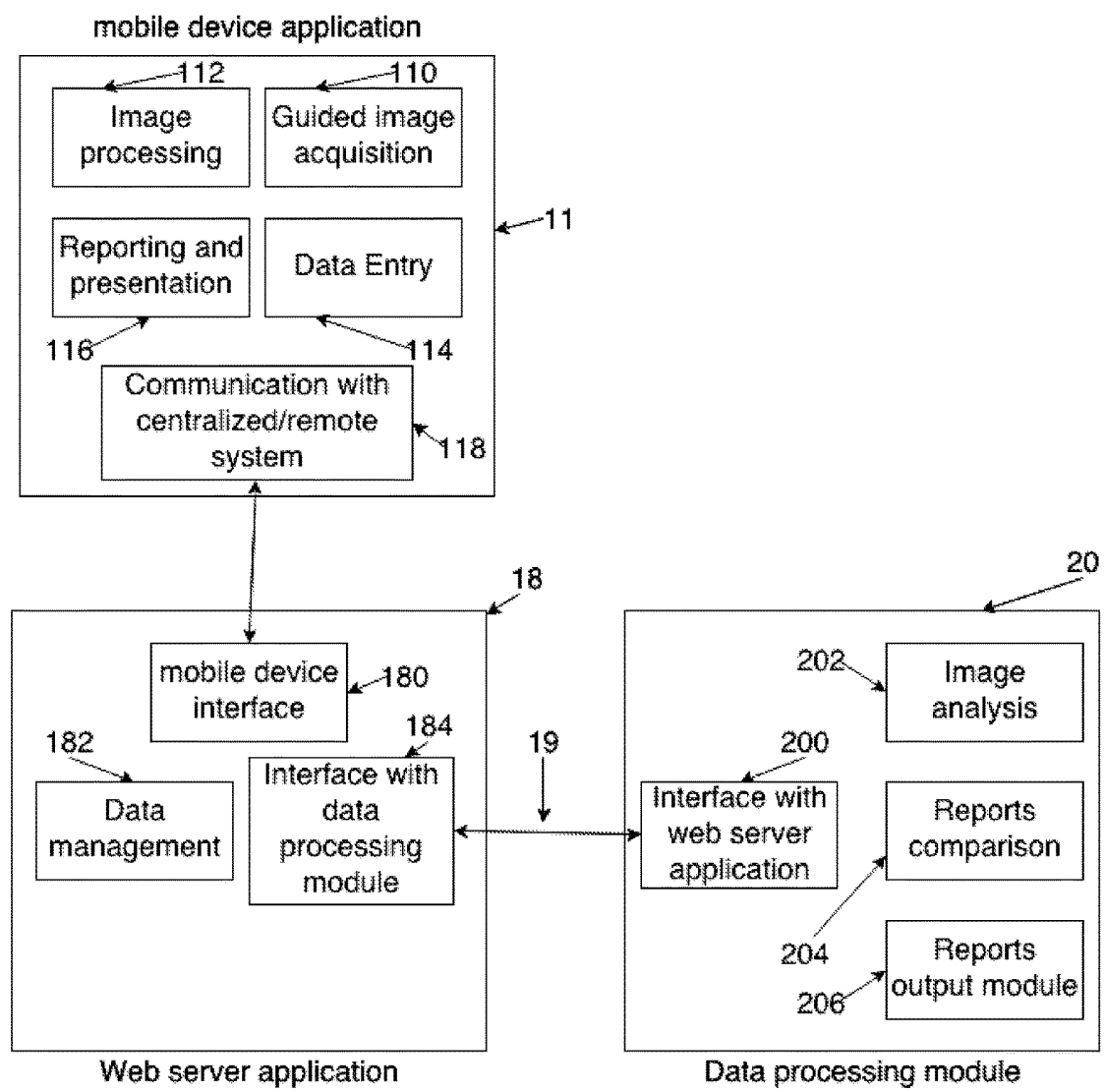
FIG. 2—a simplified block diagram of an exemplary software product (comprising a mobile software application) for performing the proposed method.

FIG. 2 shows an exemplary macro-structure of the software product for implementing the proposed technique.

The mobile device application 11 may be an independent self-contained software product comprising the following functional program blocks:
  Guided image acquisition 110 (Code for receiving images associated with the object/vehicle, operator, physical location, and other related information);
  Image processing 112 (Code for analyzing data associated with the object/vehicle for detection of surface features on a single image);
  Data entry 114 (Code for accumulating additional information related to the case and attaching it to the set of images and data processing results);
  Report creation and presentation 116 (Code for presenting various kinds of reports to system operator about surface features on the object/vehicle body).
  Interface block 118 (Code providing means of communication with a remote/centralized system, which system is an optional though a preferred part of the whole system).

The software product may further comprise another self-contained software product—a web server application 18 which may belong to a provider of the proposed inventive service, or to another service provider, and be in communication with the mobile device application 11. The web server application 18 comprises:
  Interface block 180, providing code for communication with a mobile device(s) such as 11,
  Data management block 182, comprising code providing means of managing data attached to any reference set (unique identification of the object, physical location, and the like. Management includes storage, lookup, retrieval, backup, etc.
  Interface block 184, with program means for communication with a data processing module 20.

The module 20 may be a part of the server application 18, but may be a separate application or a separate physical server, and be connected to module 18 using standard inter-process or inter-machine communication means (19). However, modules 18 and 20 may be located on the same server at the same physical location.

The module 20 may be located at a service company, for example, an insurance company, a car rental company, police, a shopping center, etc. The module 20 of the software product comprises:
  Interface block 200, with the code providing means of communication of the data management/processing module 20 with the web server application 18.
  Block for image analysis 202, providing code of data processing for the purpose of detection of surface features on a single image;
  Block for reports comparison/generation 204, providing code for generation of reports and comparing suitable images and results of sets of reports, and for generating a report of comparison.
  Block 206 for the reports' outputting/displaying (Program code for outputting reports of the data processing module 20).

Figure 3:
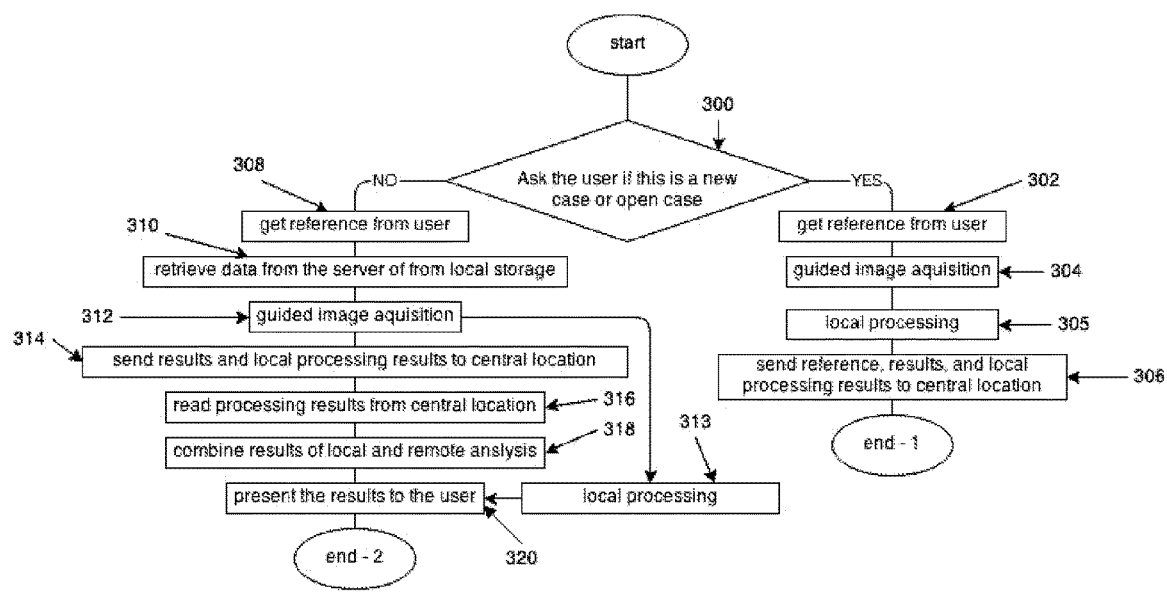
FIG. 3—is an exemplary flow chart of one version of the proposed method.

FIG. 3 describes an exemplary flow chart of one version of the proposed method, initiated by a user of a mobile device. When the mobile software application is started, it first checks whether a new case is to be opened, or whether an open case already exists (block 300). It may show the list of open cases and allow the user to select one for processing/closing the case.

If a new case is to be opened (YES), the application receives indication of a reference from the user (block 302). In terms of the present description and claims, the word "reference" used here and below should be understood as an "additional reference" or as an "earlier reference". The reference is understood as a set of images of the object of interest (for example, a predetermined standard set of images of a new car of a specific model and color). The reference set may be downloaded by the user, and installed in the software application by a service provider, etc. The reference set can be downloaded from a central storage/processing location via Internet, or be taken from a local storage/processing location if the case was opened there, for the same object.

The software application then starts providing guidance to the image acquisition, the user makes suitable photographs by the camera of the mobile device, upon which the application stores the images in the mobile device (block 304).

The suitable images obtained as a result of the guidance, should be maximally close to images of the reference set, and there are machine learning methods (morphological, classifying, etc.) teaching how to adjust the camera and the lighting to achieve the maximal similarity. The stored images along with their related data may then be processed in the mobile device (block 305). Alternatively, any information item or combination thereof (the images, the reference, the local processing results) may be sent to a remote/central location (306). Operator "End 1" indicates that the new case has been opened, and the real images & the processing results concerning the new case are stored in the mobile device and/or in a remote location.

If block 300 defines that the case is not new (NO), application asks for a reference from the user, and the user may indicate any of the available previous references related to that case (block 308, similar to block 302). Block 310 then retrieves the reference data either from the local storage (mobile device), or from a server (for example, from the central location which was updated by 306). Blocks 312 and 304 provide guidance to the user for proper image acquisition. Block 304 may use a generic reference like a generic car contour. Block 312 may use previously taken images as a guide for the current images acquisition. The images and the reference may be processed in the mobile device (block 313) and then may be sent either separately or together with the local processing results to a central location (block 314). (However, results of the local processing may be presented to the user as a local report (block 313 to block 320), which may have a separate value, for example for further handling of the case by the user himself/herself.)

The software application may then read previous processing results, say from the central location (block 316), and combine results of the local and the remote analysis (block 318). The combined results may be presented to the user as a combined report (block 320). The combined version of the method terminates with the operator End2.

Examples of performing specific method steps:
The step of obtaining the images with the guidance of the mobile application may be performed as follows.
The user may be guided by the application to adjust an actual camera position and direction to match the previous images taken of the same vehicle.
For example, the user/operator is being shown guides on the screen directing him to position the vehicle on the frame. Once the optimal possible position occurs the image is being acquired. Decision about optimal position may be done either by the operator manually by instructing the mobile device to acquire the image or automatically by the apparatus itself. Once the image is acquired, the apparatus may direct the user to take another image under different conditions (physical location, lightning, camera position) or end the process if enough data has been acquired for the defect assessment.
Examples of guides used during the process may be: a contour of a generic vehicle, a semitransparent prior image of the same vehicle, a semi-transparent image of a similar vehicle form (identified by the car type, make or model).
The guidance to the user may be provided by displaying a feedback on the device, to indicate good/bad matching between the previous (reference) and actual images taken.
The step of obtaining the images may also include dynamically assessing quality of the acquired images. Such an assessment may be used to give instant feedback to the operator/user and, if needed, require the operator to take another image under different conditions such as, different lightning conditions, stable shot, better images overlap between "before" image and current one, or adjusted angle. Nevertheless, the user may also decide himself/herself whether the actual image is suitable for analysis overriding the automatic method. Optionally, the user can manually add additional locations in which he/she detects defects that the system did not identify, or delete defects that the system might have identified wrongly.

The step of transferring of data on the set of images may comprise transmission of that data to a central storage/processing location. The images taken by the user/operator may be transmitted to the central storage location along with additional information related to the same image data. This additional ("related") data may include unique identifier of the vehicle to which the current transmission relates, time and place of taking the images, and may also include results of local processing. The local processing may include a possibility of editing images/reports by the operator. The editing should preferably be limited to removal of excessive information on "quasi-defects" (for example, information related to stickers, dirty spots, illumination artifacts etc. on a vehicle body).

Alternatively or in addition to the step of transferring the data to the central location, the acquired image data may be managed locally. The images may be stored locally on the acquiring (mobile) device alongside with so-called meta information ("related data") corresponding to these images. For example, the meta-data comprises: physical location, unique identification of the vehicle, and other information relevant to the case. List of all available images and their information may be presented to the operator/user on the device graphical interface. The mobile device will be capable to present all the data stored locally on the device. The apparatus will allow deletion of the case. The apparatus may have an optional predefined setting, which will define amount of time for data to be stored locally, after which the data may be purged automatically. The apparatus may have an optional locking of data for vehicles that blocks the apparatus from purging specific data related to specific vehicle, operator, geographical location or any other characteristics.

The step of processing and analyzing the image data at a central storage location may comprise specific management of the acquired data at that central location. For example:
The data is stored alongside with the meta information ("related data"). It can be searched by various parameters: physical location, vehicle unique identification, operator identification and other fields. The data may be retrieved from that central location using a vehicle/case identifier. Standard authentication and authorization mechanisms can be used to allow the data access.
The processing/analysis may be activated by a user/automatically at the central storage/processing location upon completion of data acquisition by the mobile device. The data analysis may be independent from the subsequent data transfer and may occur in parallel.
The image data analysis may comprise image processing techniques and or machine learning classifier techniques to compare the current and the prior images. Regions in the current image that have changed from the last inspection may be thus identified. For example, a morphological image processing technique or a classifier technique to compare the current and the prior images may be employed. In other versions of the method (application), different techniques to compare the images may be utilized. A difference between the current and the prior images may be classified as significant if the differences (for example, circumference, size, location, texture, color, etc.) are above a certain pre-set or adaptive threshold. Minor defects or artifacts in the current image compared to the prior image may or may not be classified as significant, depending upon the threshold value mentioned above. For example, features on the images obtained due to stickers, dirty spots, highlights on a vehicle body, may be considered artifacts.

The step of generating/outputting a report may comprise one or more of the following: classifying any difference/defect/damage in various degrees of severity, using various terms for types of defects (change of color, change of shape, scratch, dent, bump, etc.), indicating coordinates of the damage on the object, for example on a vehicle body.

It should be appreciated that while the invention has been described with reference to specific examples and drawings, other versions of the method may be proposed which should be considered part of the invention whenever defined by the claims, which follow.

The invention claimed is:

1. A method for image acquisition and management, by utilizing a mobile device equipped with a camera and with a mobile software application;
the method comprises the following steps enabled and/or supported by the software application:
providing, by the mobile software application, guidance to an operator for guided making, by the camera, a set of one or more images of an object, wherein the guidance comprises presenting, by the mobile software application to the operator, one or more respective angles suggested by the mobile software application for obtaining said set of one or more images properly registering currently existing visible features of said object,
obtaining said set of images,
storing said set of obtained images as a current reference set, along with its related data, in at least one storage/processing location being selected from a list comprising the mobile device and a remote location,
analysis including steps of:
comparing said current reference set with an additional reference set, the additional reference set being selected at least from the following two additional reference sets:
an earlier reference set of said object,
a later reference set of said object;
based on said comparison, creating a report concerning differences, if any, between the obtained set of images being the current reference set, and the selected additional reference set, and
displaying the report in at least one of said storage/processing locations.

2. The method according to claim 1,
wherein the guidance is performed based on the earlier reference set for said object, the earlier reference set and its corresponding related data being provided in advance and being accessible by said software application; and
wherein said guidance is aimed at obtaining said set of images being maximally close to those in the earlier reference set, while said guidance is simultaneously aimed at properly registering the currently existing visible features of said object.

3. The method according to claim 1, wherein the earlier reference set comprises one of the following two sets of images comprising one or more images provided before said current reference set, and accompanied with its related data:
a default/etalon set of one or more images created for objects of the type to which said object belongs;
a set of one or more images of said object, obtained and stored in said at least one storage/processing location.

4. The method according to claim 1, wherein said later reference set comprises a set of one or more images of said object, obtained later than said current reference set, stored in said at least one storage/processing location and accompanied with its related data.

5. The method according to claim 1, wherein the object is a vehicle body.

6. The method according to claim 1, further comprising:
preliminarily providing one or more said additional reference sets to be accessible by the mobile software application,
selecting an additional reference set from said one or more additional reference sets for further processing.

7. The method according to claim 1, comprising creating, for the same object, more than one said reports respectively based on different more than one additional reference sets, the method further comprising comparing said more than one reports.

8. The method according to claim 1, wherein said guidance is provided by directing the operator, via the display of the mobile device, to adjust an actual camera position and direction so as to maximally match the selected additional reference set.

9. The method according to claim 1, comprising transferring the obtained set of images, along with the related data, to a remote storage/processing location by means of a communication network.

10. The method according to claim 1, further comprising:
preliminarily providing the mobile device with said camera and said mobile software application,
activating the mobile software application,
obtaining said set of one or more images of the object by using said camera with the guidance of said mobile software application,
storing the obtained set of images as a current reference set in the mobile device and/or in a remote storage/processing location,
selecting an additional reference set from one or more available additional reference sets,
processing said current set of images by analyzing thereof based on the selected additional reference set,
generating a report on differences between said current reference set and the selected additional reference set, and
displaying the report in the mobile device and/or in the remote storage/processing location.

11. The method according to claim 1, wherein at least one of the storage/processing locations is either on a remote central server, or on a server of a dedicated company providing at least one service related to the object and selected from a non-exhaustive list comprising: support to the software application, manufacturing, trade/sales, transportation, rent, repair, insurance, guard, parking, legal services.

12. The method according to claim 1, further comprising a step of forwarding the obtained report to at least one company or institution providing services related to the object.

13. A software product stored on an appropriate non-transitory computer readable storage medium, comprising computer implementable instructions and/or data for carrying out the method according to claim 1, so that the software is capable of enabling operations of said method when used in a computer system.

14. The software product according to claim 13, being a mobile software application, wherein the storage medium is the memory of the mobile device.

15. The software product according to claim 13, specifically designed for detecting defects on the object being a vehicle body.

16. The software product according to claim 13, provided with means for establishing communication with relevant companies or institutions, for filing to them the report.

17. A computerized system for implementing the method according to claim 1.

18. A system comprising a mobile device with the software product according to claim 13, installed in the memory of the mobile device.

19. The system according to claim 18, additionally comprising a storage/processing server at a remote location, connected with the mobile device via communication lines.

20. A computerized system for image acquisition and management, the system comprising
 a mobile device equipped with a camera and with a mobile software application, the system also including at least one storage/processing location being selected from a list comprising the mobile device and a remote location;
 the system being operative to perform the following steps enabled and/or supported by the software application:
 providing, by the mobile software application, guidance to an operator for guided making a set of one or more images of an object using the camera, wherein the guidance comprises suggesting, by the mobile software application to the operator, one or more angles for obtaining said set of one or more respective images properly registering currently existing visible features of said object,
 obtaining said set of images, and
 storing said set of obtained images as a current reference set, along with its related data, in said at least one storage/processing location, the analysis including steps of:
 comparing said current reference set with an additional reference set, the additional reference set being selected at least from the following two additional reference sets:
 an earlier reference set of said object,
 a later reference set of said object;
 based on said comparison, creating a report concerning differences, if any, between the obtained set of images being the current reference set, and the selected additional reference set, and
 displaying the report in at least one of said storage/processing locations.

21. A method for image acquisition and management, by utilizing a mobile device equipped with a camera and with a mobile software application;
 the method comprises the following steps enabled and/or supported by the software application:
 providing guidance to an operator for making, by the camera, a set of one or more images of an object, so as to obtain said set of images using respective one or more angles suggested by the software application for properly registering currently existing visible features of said object,
 obtaining said set of images,
 storing said set of obtained images as a current reference set, along with its related data, in at least one storage/processing location being selected from a list comprising the mobile device and a remote location,
 the method further comprises analysis including steps of:
 comparing said current reference set with an additional reference set, the additional reference set being selected at least from the following two additional reference sets:
 an earlier reference set of said object, and
 a later reference set of said object;
 based on said comparison, creating a report concerning differences, if any, between the obtained set of images being the current reference set, and the selected additional reference set,
 displaying the report in at least one of said storage/processing locations.

22. The method according to claim 21, wherein the guidance is performed based on the earlier reference set for said object, the earlier reference set and its corresponding related data being provided in advance and being accessible by said software application; and
 wherein said guidance is aimed at obtaining said set of images being maximally close to those in the earlier reference set, while said guidance is simultaneously aimed at properly registering the currently existing visible features of said object.

23. The method according to claim 21, wherein the earlier reference set comprises one of the following two sets of images comprising one or more images provided before said current reference set, and accompanied with its related data:
 a default/etalon set of one or more images created for objects of the type to which said object belongs;
 a set of one or more images of said object, obtained and stored in said at least one storage/processing location.

24. The method according to claim 21, wherein said later reference set comprises a set of one or more images of said object, obtained later than said current reference set, stored in said at least one storage/processing location and accompanied with its related data.

25. The method according to claim 21, wherein the object is a vehicle body.

26. The method according to claim 21, further comprising:
 preliminarily providing one or more said additional reference sets to be accessible by the mobile software application,
 selecting an additional reference set from said one or more additional reference sets for further processing.

27. The method according to claim 21, comprising creating, for the same object, more than one said reports respectively based on different more than one additional reference sets, the method further comprising comparing said more than one reports.

28. The method according to claim 21, wherein said guidance is provided by directing the operator, via the display of the mobile device, to adjust an actual camera position and direction so as to maximally match the selected additional reference set.

29. The method according to any claim 21, comprising transferring the obtained set of images, along with the related data, to a remote storage/processing location by means of a communication network.

30. The method according to claim 21, further comprising:
preliminarily providing the mobile device with said mobile software application, and
activating the mobile software application.

31. The method according to claim 21, wherein at least one of the storage/processing locations is either on a remote central server, or on a server of a dedicated company providing at least one service related to the object and selected from a non-exhaustive list comprising: support to the software application, manufacturing, trade/sales, transportation, rent, repair, insurance, guard, parking, legal services.

32. The method according to claim 21, further comprising a step of forwarding the obtained report to at least one company or institution providing services related to the object.

33. A software product stored on an appropriate non-transitory computer readable storage medium, comprising computer implementable instructions and/or data for carrying out the method according to claim 21, so that the software is capable of enabling operations of said method when used in a computer system.

34. The software product according to claim 33, being a mobile software application, wherein the storage medium is the memory of the mobile device.

35. The software product according to claim 33, specifically designed for detecting defects on the object being a vehicle body.

36. The software product according to claim 33, provided with means for establishing communication with relevant companies or institutions, for filing to them the report.

37. A computerized system for implementing the method according to claim 21.

38. A system comprising a mobile device with the software product according to claim 33, installed in the memory of the mobile device.

39. The system according to claim 38, additionally comprising a storage/processing server at a remote location, connected with the mobile device via communication lines.

40. A computerized system for image acquisition and management, the system comprising
a mobile device equipped with a camera and with a mobile software application;
the system also comprising at least one storage/processing location being selected from a list including the mobile device and a remote location;
the system being operative to perform the following steps enabled and/or supported by the software application:
providing guidance to an operator for making, by the camera, a set of one or more images of an object, so as to obtain said set of images using respective one or more angles suggested by the software application for properly registering currently existing visible features of said object,
obtaining said set of images,
storing said set of obtained images as a current reference set, along with its related data, in at least one storage/processing location,
comparing said current reference set with an additional reference set, the additional reference set being selected at least from the following two additional reference sets:
an earlier reference set of said object, and
a later reference set of said object;
based on said comparison, creating a report concerning differences, if any, between the obtained set of images being the current reference set, and the selected additional reference set, and
displaying the report in at least one of said storage/processing locations.

41. A method for image acquisition and management, by utilizing a mobile device equipped with a camera and with a mobile software application;
the method comprises the following steps enabled and/or supported by the software application:
providing, by the mobile software application, guidance to an operator for guided making, by the camera, a set of one or more images of an object, wherein the guidance comprises presenting, by the mobile software application to the operator, one or more respective angles suggested by the mobile software application for obtaining said set of one or more images properly registering currently existing visible features of said object,
obtaining said set of images,
storing said set of obtained images as a current reference set, along with its related data, in at least one storage/processing location being selected from a list comprising the mobile device and a remote location,
preliminarily providing the mobile device with said camera and said mobile software application,
activating the mobile software application,
obtaining said set of one or more images of the object by using said camera with the guidance of said mobile software application,
storing the obtained set of images as a current reference set in the mobile device and/or in a remote storage/processing location,
selecting an additional reference set from one or more available additional reference sets, processing said current set of images by analyzing thereof based on the selected additional reference set,
generating a report on differences between said current reference set and the selected additional reference set, and
displaying the report in the mobile device and/or in the remote storage/processing location.

* * * * *